United States Patent [19]

Ellenberg et al.

[11] Patent Number: 4,810,250
[45] Date of Patent: Mar. 7, 1989

[54] OSTOMY APPARATUS

[76] Inventors: William J. Ellenberg, Box 189, Walters Rd., Oriskany, N.Y. 13424; William C. Ellenberg, 251 Woodland Ave., (Apt. 1D), Yonkers, N.Y. 10703

[21] Appl. No.: 518,055

[22] Filed: Jul. 28, 1983

[51] Int. Cl.[4] ............................................. A61M 31/00
[52] U.S. Cl. ........................................ 604/277; 604/334
[58] Field of Search ............... 604/333, 334, 277, 335; 222/211; 206/363, 438, 570, 571, 572

[56] References Cited

U.S. PATENT DOCUMENTS

| 657,463 | 9/1900 | Simpson | 206/572 |
|---|---|---|---|
| 2,054,535 | 9/1936 | Diack | 604/333 |
| 2,502,742 | 4/1950 | Nothdurft | 604/333 |
| 2,689,567 | 9/1954 | Welch | 604/333 |
| 2,902,036 | 9/1959 | Perry | 604/334 |
| 3,690,320 | 9/1972 | Riely | 604/333 |
| 3,851,649 | 12/1974 | Villari | 206/571 |
| 3,910,274 | 10/1975 | Nolan | 604/333 |
| 4,286,735 | 9/1981 | Sneider | 222/211 |
| 4,479,818 | 10/1984 | Briggs et al. | 604/333 |

Primary Examiner—C. Fred Rosenbaum
Assistant Examiner—J. L. Kruter
Attorney, Agent, or Firm—Wall and Roehrig

[57] ABSTRACT

An ostomy kit including a controllable vent device for releasing gas pressure that builds up in an ostomy collection pouch. The vent device comprises a flexible tube that is long enough to extend from the pouch to a point above the wearer's waist and a tube clamp mounted on the tube near its upper end. The clamp normally closes the tube but can be easily opened through the clothing of the wearer to release the gas when pressure starts to build up. The ostomy kit also includes a bottom feed squeeze bottle having a one-way air inlet valve in its top and a nozzle that is adapted to be connected to the upper end of the vent device tube for flushing out the ostomy pouch when the tube clamp is open. The kit also includes a chute member that coacts with the squeeze bottle in rinsing the stoma area after the pouch has been disconnected from the area.

3 Claims, 1 Drawing Sheet

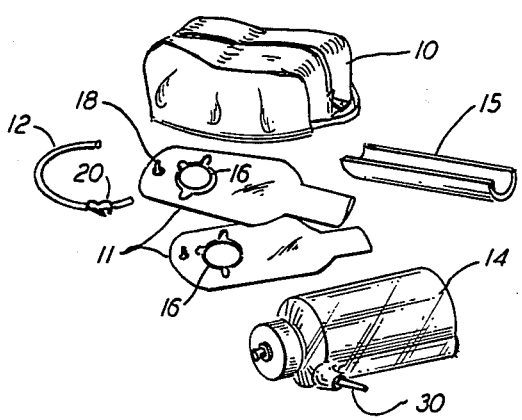
FIG. 1
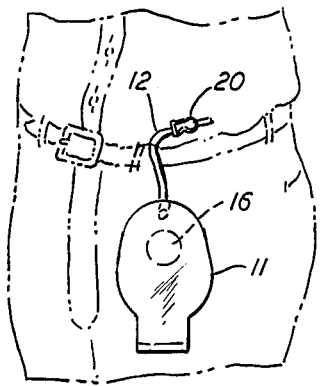
FIG. 2
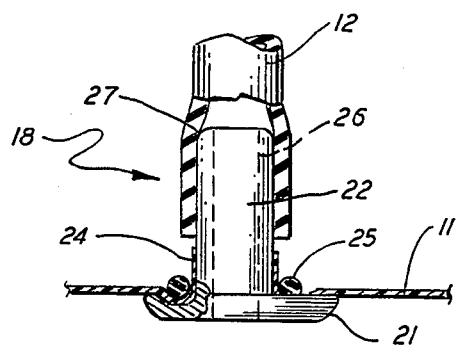
FIG. 3
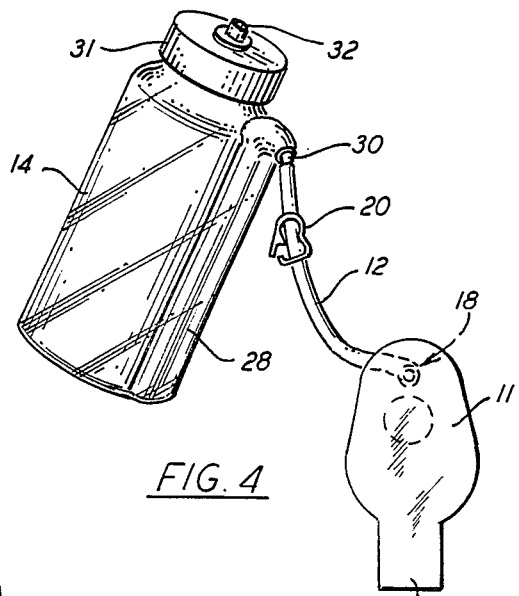
FIG. 4
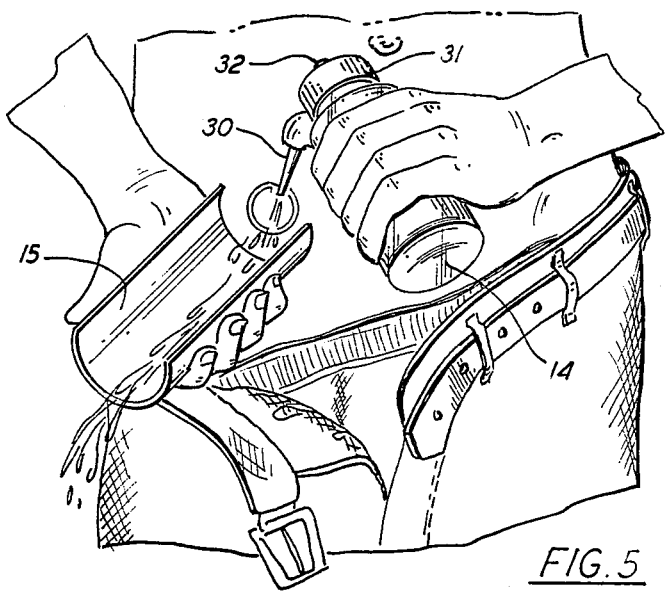
FIG. 5
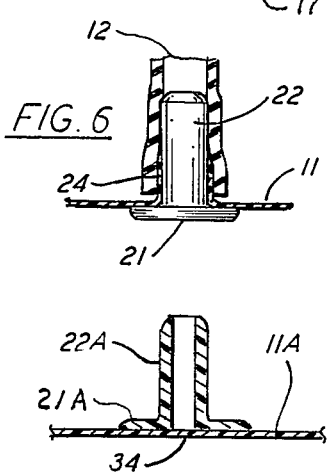
FIG. 6
FIG. 7

OSTOMY APPARATUS

BACKGROUND OF THE INVENTION

This invention relates generally to post surgical appliances, and has particular reference to novel post surgical apparatus for persons who have undergone ostomy surgery such as a colostomy or ileostomy. A particular feature of the invention is the provision of a controllable device for releasing gas pressure in an ostomy collection pouch.

Persons who have had ostomy surgery must wear a collection pouch that is attached to the body over the stoma to collect excretory substances and fluids. A number of different pouches and the means for attaching them have been developed heretofore and are well known in the art. Obviously, the need to wear such a pouch creates problems for the wearer, and this is particularly so for those seeking to resume a normal active life including such things as automobile and aircraft travel for business and social purposes.

One problem that ostomy patients, or ostomates, have had in the past is that of a gas build-up in the pouch. This can happen at any time and causes the pouch to inflate to the point where it makes a noticeable bulge beneath the clothing of the wearer. To relieve the gas pressure, which may also cause the ostomate discomfort, the usual procedure heretofore has been to partially disconnect the pouch from the attachment ring affixed to the wearer which allows the gas to vent. This requires partial disrobing in a rest room or other private place and may not be at all convenient if the ostomate is travelling or attending a business conference, or the like.

In attempting to solve the gas build-up problem in the past, ostomates have tried perforating the pouch with a pin but this does not achieve the desired relief and such gas venting as does occur is not under the ostomate's control. The only prior art known to the applicants that addresses itself directly to the gas build-up problem is U.S. Pat. No. 4,203,445 granted May 20, 1980 to Jessup et al. for a Gas Venting Filter Assembly for Collection Device, together with the prior patents cited in the Jessup patent. The Jessup assembly is used with an ostomy pouch and provides for a deodorizing filter designed for the free flow of gas therethrough. The filter coacts with a slit in the pouch wall to vent the gas. With the Jessup filter assembly, the venting is continuous rather than under the control of the wearer which is a disadvantage because if the filter does not function properly it can cause embarrassment to the wearer.

Another problem for ostomates arises when rinsing the stoma area after disconnecting the pouch. If the person is clothed, the clothes usually get wet; in addition, the task can be particularly awkward in a public lavatory or when using a bathroom sink that is set in a countertop.

SUMMARY OF THE INVENTION

The present invention provides an ostomy kit that is designed to help the ostomate with his problems, a particular feature of the kit being a controllable venting device for releasing gas pressure that builds up in an ostomy collection pouch. The gas venting device comprises a vent head in a wall of the pouch, a flexible tube that is long enough to extend from the vent head to a point above the pouch wearer's waist, and a tube clamp mounted on the tube near its upper or free end. The lower end of the tube is connected in a gas-tight manner to the vent head and the latter is provided with a through passage so that gas from the pouch can enter the tube. The clamp normally closes the upper end of the tube but can be easily manipulated through the clothing of the wearer to open the tube and release the gas when pressure starts to build up.

The ostomy kit disclosed herein also includes a bottom feed squeeze bottle having a one-way air inlet valve in its top and a nozzle that is adapted to be connected to the upper end of the venting device tube. With this arrangement, the bottle can be used to flush out the ostomy pouch when the tube clamp is open. The kit also includes a chute member that coacts with the squeeze bottle in rinsing the stoma area after the pouch has been disconnected from the area. Thus, clean water in the bottle can be directed toward the area by means of the nozzle and then carried by the chute member into a toilet bowl, the task being performed with a minimum of difficulty and without getting clothing wet.

BRIEF DESCRIPTION OF THE DRAWINGS

FIG. 1 is a laid out perspective view of an ostomy kit embodying the invention;

FIG. 2 is a front elevation of an ostomy pouch together with the gas venting device of the invention, the wearer of the device being partially shown in phantom lines to better illustrate the application of the venting device;

FIG. 3 is an enlarged side elevation, partly in section, of the vent head portion of the gas venting device;

FIG. 4 is a perspective view of the squeeze bottle connected to the gas venting tube for rinsing the pouch;

FIG. 5 is a front perspective view showing the squeeze bottle and chute member as they are used to cleanse the stoma area;

FIG. 6 is a side elevation, partly in section, of a modified form of the vent head; and FIG. 7 is a vertical sectional view through another modified form of the vent head.

DESCRIPTION OF THE PREFERRED EMBODIMENTS

Having reference now to the drawings, and with particular reference to FIG. 1, the ostomy kit is essentially comprised of a carrying case 10, a supply of collection pouches 11 of conventional construction, a flexible tube 12 for the gas venting device, a squeeze bottle 14 and a chute member 15. The pouches shown are provided with stoma attachment rings 16 which engage a corresponding part on the wearer. As purchased, the outlet ends 17 of the pouches are open (see FIG. 4) and before using they are folded and sealed with a suitable clasp (not shown) in a known manner (see FIG. 2).

The gas venting device includes a vent and flush head generally indicated at 18 in FIG. 3, the flexible tube 12 and a simple hose clamp 20 to be described. The vent head 18 passes through a wall of the pouch to provide a sealed gas release passage therethrough and is located between the attachment ring 16 and top of the pouch as best shown in FIGS. 1 and 2. It is contemplated that vent heads as shown in FIG. 3 will be applied to the pouches by the user of the kit but they may alternatively be applied by the pouch manufacturer.

In the embodiment of the invention shown, the vent head is an aluminum element similar to a pop rivet and has a head portion 21 and shank portion 22, FIG. 3. The shank portion passes through a hole in the pouch wall that has a smaller diameter than the outside diameter of the shank portion and this causes the pouch material to stretch and form a tight collar 24 around the shank. The collar 24 is encircled by a tightly fitting O-ring 25 as shown, and with this arrangement the pouch and vent head are secured together in a gas tight manner.

The vent head 18 has a longitudinal passage 26, FIG. 3, therethrough for the release of gases that build up in the pouch. The shank portion 22 of the vent head is connected to one end of the flexible tube 12, the tube having a slightly smaller inside diameter than the outside diameter of the shank whereby the tube engages the shank in a gas tight manner. In this connection, the outer end of the shank is formed with a radius 27 to facilitate engagement of the parts. Tube 12 is preferably latex laboratory tubing with an inner diameter of $\frac{1}{8}''$ to 3/16'', and in accord with the invention it is long enough to extend from the vent head on the pouch to a point above the waist of the wearer, see FIG. 2.

Mounted on the tube 12 near its free or upper end is the hose clamp 20 which is a one piece, normally closed mini clamp of conventional design. This clamp has an open position shown in FIGS. 1 and 4 which permits fluid to pass through the tube and a closed position shown in FIG. 2 which prevents the passage of fluid. Clamp 20 can be opened and closed very easily with the fingers of one hand and this can be done through one or more layers of clothing. The venting of gas that builds up in the pouch is therefore totally under the control and discretion of the pouch wearer and can be accomplished without the need to partially disrobe.

When it is desired to cleanse the collection pouch 11 without detaching it from the wearer, this can be done in a convenient manner using the squeeze bottle 14, see FIG. 4. Bottle 14 is a commercially available bottom feed bottle and when it is squeezed, liquid at the bottom of the bottle is forced up through an exterior tube 28 and out through a nozzle 30 at the upper end of the tube, the bottle being maintained in a substantially upright position during the operation.

In cleaning the pouch 11, the upper end of the gas venting tube 12 is connected to the squeeze bottle nozzle 30, FIG. 4, and the clamp 20 is opened. Then, standing above a toilet bowl or the like, the bottom of the pouch 11 is opened and the bottle, which was previously filled with clean water, is squeezed forcing the water down the tube 12 and through the pouch whereby the latter is cleansed. In this connection, a very important and novel feature of the squeeze bottle is the provision in its top closure or cap 31 of a one-way air intake valve 32. The valve permits replacement air to enter the bottle through the cap each time it is squeezed; without the valve, matter in the pouch would tend to return to the bottle through the tube 12 which obviously would be counter productive.

At times when the collection pouch 11 has been detached altogether from the wearer and it is desired to rinse the stoma area, this can be accomplished with a minimum of difficulty using the squeeze bottle 14 and chute member 15, see FIG. 5. Thus, one end of the chute is held against the body below the stoma as shown and the other end is positioned over the edge of a sink or toilet. The squeeze bottle can then be used to thoroughly rinse the stoma area with a controlled jet of water that is carried away by the chute without spilling and without the user having to get himself in an awkward position.

FIG. 6 illustrates a modification of the vent and flush head wherein the O-ring 25 shown in FIG. 3 is eliminated. In many commercially available pouches 11 the pouch material makes a tight enough seal with the vent head shank 22 so that an O-ring is not necessary. Moreover, the end of tube 12 can be brought into overlapping engagement with the collar 24 as shown and this further insures that the parts are secured together in a gas tight manner.

FIG. 7 illustrates another modification of the vent and flush head. In this modification, the head is made of plastic and its head portion 21A is secured during manufacture to the outside of the pouch 11A as by sonic welding. Prior to use, a suitable aperture is made in the pouch at 34 to permit gas to vent. It will be understood that the shank portion 22A of the vent head is sufficiently rigid to permit it to be engaged with the tube 12.

From the foregoing description it will be apparent that the invention provides novel and very beneficial apparatus for those who have undergone ostomy surgery. As will be understood by those familiar with the art, the invention may be embodied in other specific forms without departing from the spirit or essential characteristics thereof.

We claim:

1. In combination with an ostomy collection pouch having a stoma attachment ring for attaching the pouch to the wearer, a gas venting device comprising a vent head extending through a wall of the pouch in sealed relation thereto, the venting device being located between the attachment ring and the upper end of the pouch, the vent head having a shank portion extending outwardly beyond the exterior of the pouch wall with a gas passage therethrough, the passage extending from the interior of the pouch to the outer end of the shank portion, a flexible tube of sufficient length to extend from the pouch to a point a short distance above the waist of the wearer, the vent head shank portion being received in one end of the tube in sealed relation thereto, and a clamp member positioned on the tube adjacent its other end, the clamp member having closed and open positions for sealing off or opening up the tube at the discretion of the wearer, the tube and clamp member being positioned beneath the clothing of the wearer so as to be concealed from view.

2. The combination defined in claim 1 together with a bottom feed squeeze bottle having a nozzle engageable with said tube other end, the bottle being operable to flush the pouch when the clamp member is in open position.

3. The combination defined in claim 2 together with a top closure for the bottle having a one-way air inlet valve therein.

* * * * *